United States Patent
Bowers et al.

(10) Patent No.: US 6,357,601 B1
(45) Date of Patent: Mar. 19, 2002

(54) ULTRAFILTRATION DEVICE AND METHOD OF FORMING SAME

(75) Inventors: William F. Bowers, Topsfield; Basil Yankopoulos, Peabody, both of MA (US); Timothy Towle, Lee, NH (US)

(73) Assignee: Orbital Biosciences LLC, Topsfield, MA (US)

(*) Notice: Subject to any disclaimer, the term of this patent is extended or adjusted under 35 U.S.C. 154(b) by 0 days.

(21) Appl. No.: 09/454,032

(22) Filed: Dec. 3, 1999

Related U.S. Application Data

(60) Provisional application No. 60/111,068, filed on Dec. 4, 1998, and provisional application No. 60/116,890, filed on Jan. 22, 1999.

(51) Int. Cl.$^7$ .............................................. B01D 29/085
(52) U.S. Cl. .................... 210/455; 210/451; 210/452; 156/272.2
(58) Field of Search .................... 210/451, 452, 210/455, 473, 477, 481; 156/272.2, 274.4, 304.6, 380.3, 380.6, 379.6; 426/77, 83

(56) References Cited

U.S. PATENT DOCUMENTS

| | | | |
|---|---|---|---|
| 2,805,164 A | * 9/1957 | Doppler | 426/77 |
| 3,082,587 A | 3/1963 | Brimberg | |
| 3,488,768 A | 1/1970 | Rigopulos | 210/23 |
| 3,801,405 A | 4/1974 | Corkery et al. | 156/306 |
| 3,980,563 A | * 9/1976 | Greutert et al. | 210/232 |
| 4,231,876 A | * 11/1980 | Zimmermann et al. | 210/232 |
| 4,458,020 A | 7/1984 | Bohn et al. | 435/296 |
| 4,522,713 A | 6/1985 | Nussbaumer et al. | 210/136 |
| 4,632,761 A | 12/1986 | Bowers et al. | 210/650 |
| 4,722,792 A | 2/1988 | Miyagi et al. | 210/360.1 |
| 4,755,301 A | 7/1988 | Bowers et al. | 210/650 |
| 4,769,145 A | 9/1988 | Nakajima | 210/321.75 |
| 5,373,620 A | 12/1994 | Zine | 29/469.5 |
| 5,460,078 A | * 10/1995 | Weller et al. | 99/295 |
| 5,647,990 A | 7/1997 | Vassarotti | 210/650 |
| 5,674,395 A | 10/1997 | Stankowski et al. | 210/321.75 |
| 5,733,449 A | 3/1998 | Bowers et al. | 210/321.6 |
| 5,863,431 A | * 1/1999 | Salzburg | 210/474 |

FOREIGN PATENT DOCUMENTS

| WO | WO9532793 | 12/1995 |
|---|---|---|

* cited by examiner

*Primary Examiner*—John Kim
(74) *Attorney, Agent, or Firm*—Nutter McClennen & Fish LLP

(57) ABSTRACT

An ultrafiltration device has a ported reservoir body, and a filter membrane sealed to the body along a closed contour surrounding the port(s) to provide a large area filtered outflow path. A frusto-conical end provides hydrostatic deadstopping with little or no wicking, greatly enhancing recovery time and efficiency. Methods of using the device rapidly isolate a predetermined amount of a desired retentate in the distal portion of the tube, and are also useful for quantitative transfer of smaller molecules and for multi-step processing of sample arrays Linear array strips of such chambers may be formed by bonding together mating halves with filter areas over the chamber ports. The vessel may include a rib to guide and orient filter during assembly, and/or a ledge or recess to engage and align the filter, assuring that the filter is precisely positioned and does not wander during manufacture and bonding. The vessels have a high filter area to volume ratio, maintain open filter surfaces and high rates of filtration throughout the spin, and are fully compatible with robotic loading, multistage operation and in situ multiwell plate filtrate and/or retentate assay or transfer. Attachment of the filter may be effected by heat welding. Preferably the vessel and filter are positioned between a press member and a heat sink and a superheated tool contacts the press member to selectively deliver a defined bolus of heat to the weld areas.

12 Claims, 13 Drawing Sheets

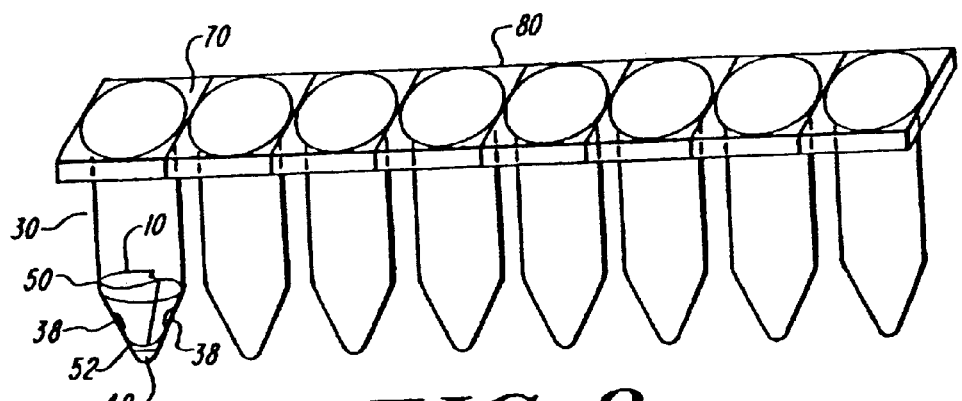
*FIG. 8*
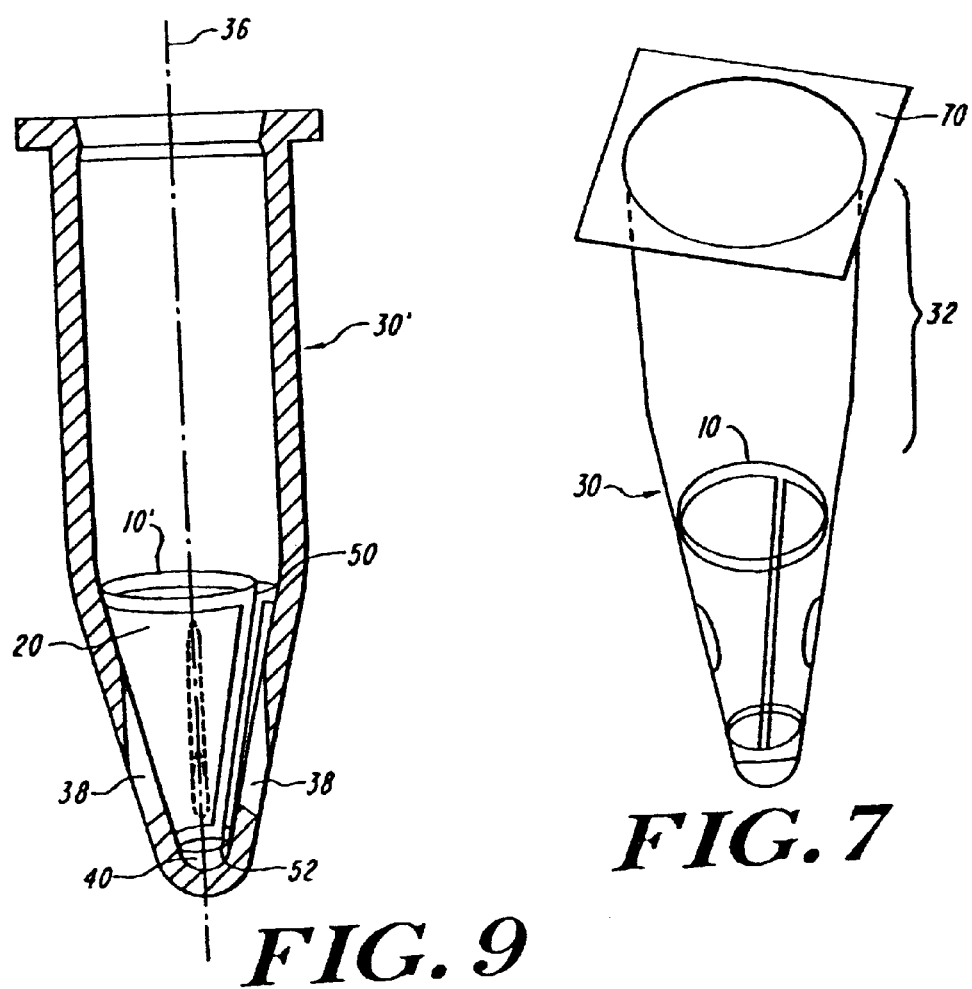
*FIG. 9*
*FIG. 7*

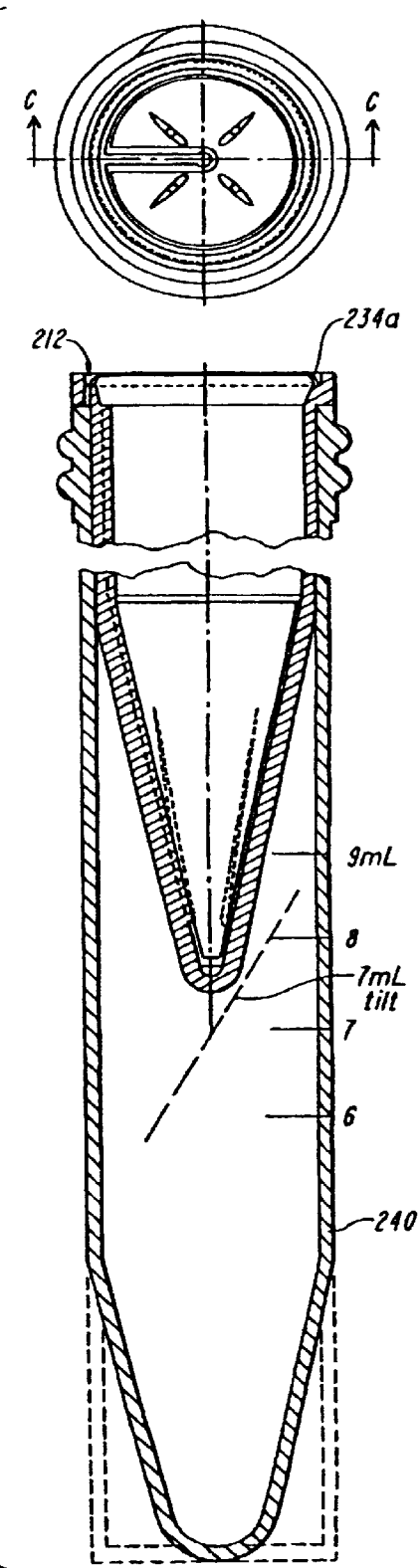
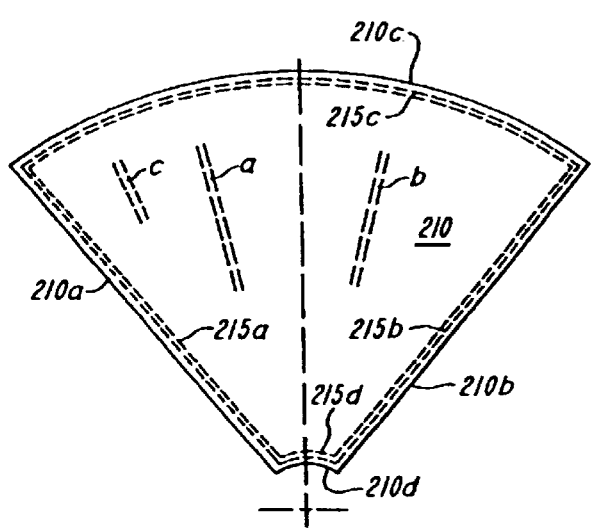
FIG. 11C
FIG. 11D

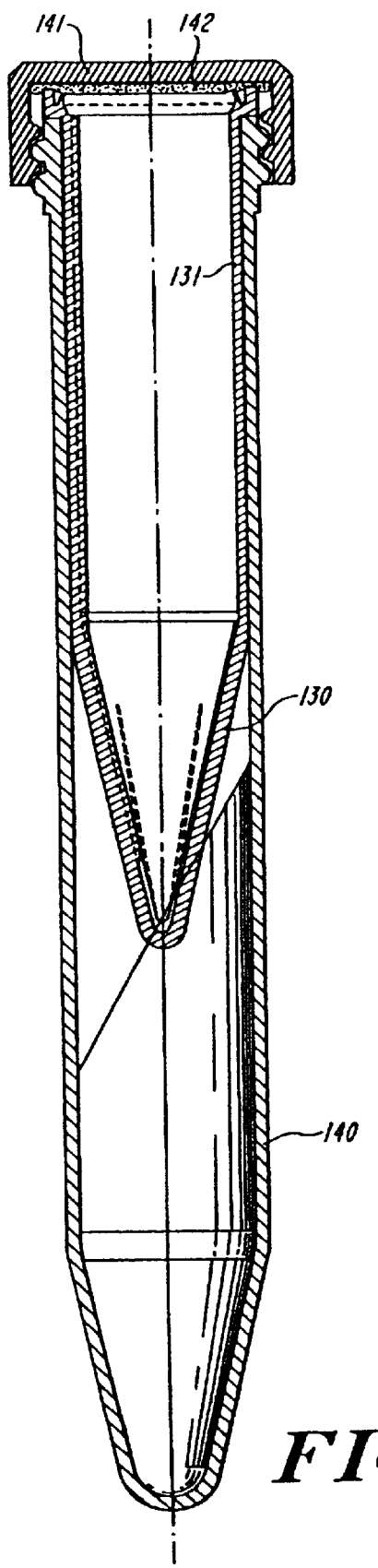
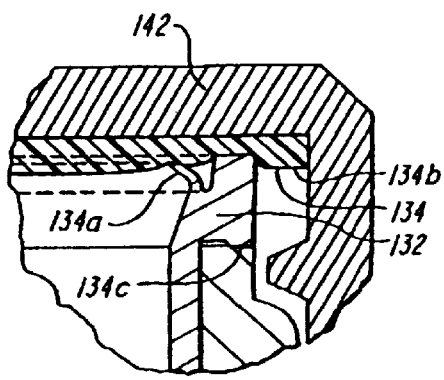
FIG. 12C
FIG. 12B

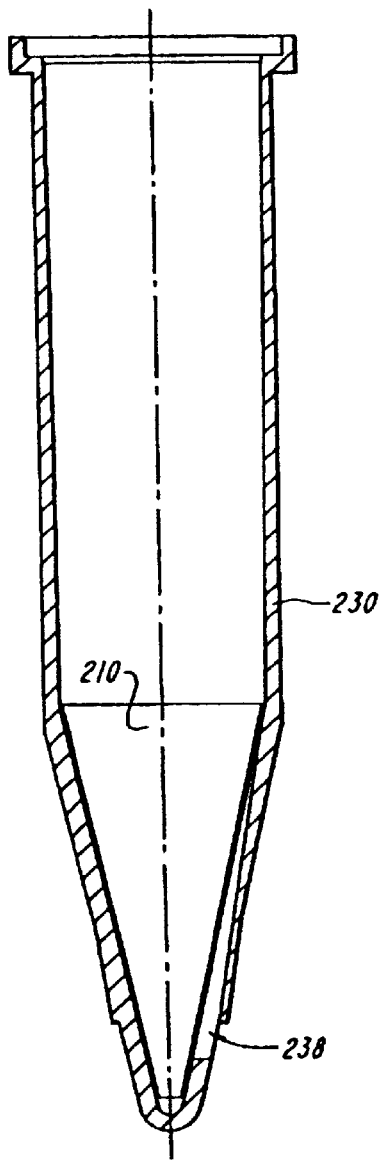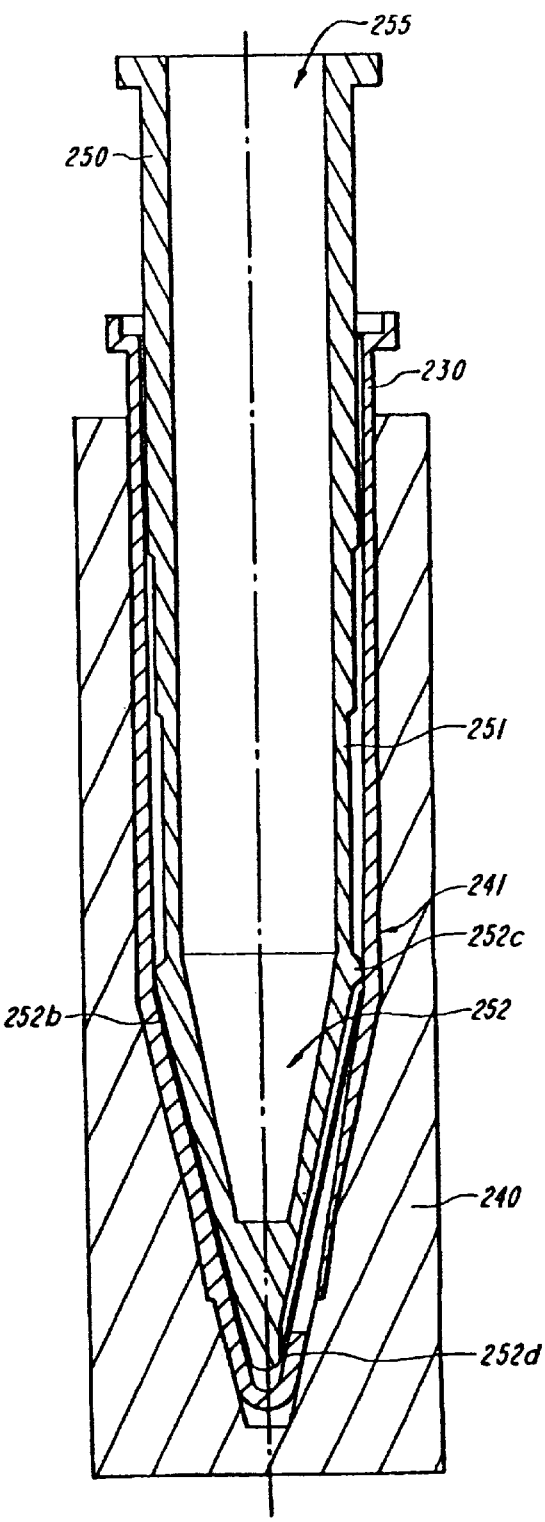
*FIG. 13A*
*FIG. 13B*

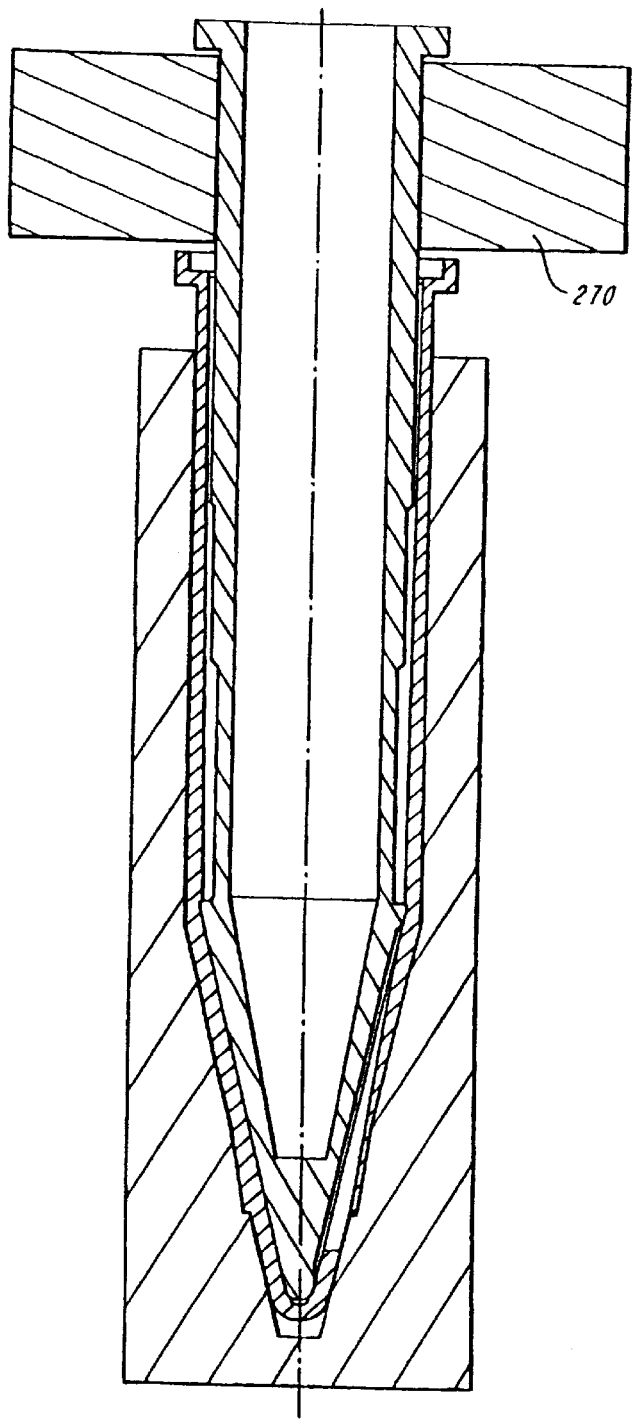
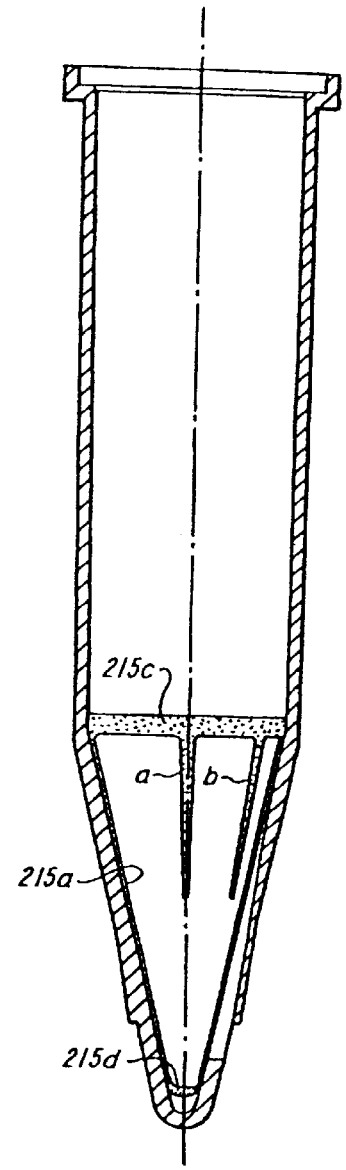
*FIG. 13E*
*FIG. 13F*

ULTRAFILTRATION DEVICE AND METHOD OF FORMING SAME

REFERENCE TO RELATED APPLICATIONS

This patent application is related to, and claims the benefit of U.S. Provisional Patent Applications No. 60/111,068 filed Dec. 4, 1998 and No. 60/116,890 filed Jan. 22, 1999, each of which is hereby incorporated by reference herein in its entirety.

STATEMENT REGARDING FEDERALLY-SPONSORED RESEARCH

A portion of the present invention was supported by NIH Grant #1 R43 RR12066-01.

BACKGROUND OF THE INVENTION

Various devices are known for isolating a retentate containing a high molecular weight material, such as DNA or protein, through centrifugal ultrafiltration. The yields and amounts of retentate achieved using these techniques vary greatly due to the size, shape and position of filter membrane, the positions of outlets and/or the presence of ledges, corners or compartments in the devices.

Often these devices have associated limitations or drawbacks. For example, a device may be ineffective to prevent filtration of retentate to near dryness, or may have a design that hinders access to, or prevents complete pipette recovery of, the retentate due to chamber geometry, surface tension spreading, or the like. Also, a device may attain only a low yield or poor separation, or may require excessive centrifuge times. Additionally, a device may be poorly adapted for, or entirely incapable of, being prepared by or being used with robotic or other automated devices. Further, a technique or device may be uneconomic due, for example, to inefficient utilization of filter membrane area, and/or to manufacturing cost, and/or to requiring a long centrifuge time.

Therefore, a need exists for a centrifugal ultrafiltration device that can be dependably manufactured and used.

There is also a need for a separation technique that is rapid, effective and amenable to automated implementation.

There is also a need for improved processes for the manufacture or assembly of filtration or concentration vessels.

SUMMARY OF THE INVENTION

One or more of the foregoing ends are achieved in accordance with the present invention by providing a separation vessel having a conical region extending to a closed tip and a port in the wall of the conical region covered by a filter. The filter has a pore size and structure such that when centrifuged, fluid material such as solvent and solutes with a molecular weight below a threshold level passes through the filter and out the port. The conical region has a cone angle that causes retentate accumulating on the inner surface of the filter to slough down into the closed tip. Advantageously, the filter covers an area substantially larger than the port and is supported by the underlying wall so that a large filter area is actively used, and also resists clogging, thus allowing fast filtration. Moreover, the conical shape, which may extend from a cylindrical proximal or upper body portion, subtends a large reservoir of material in the vessel while allowing the receiving end to be sized for retaining a relatively small or minor fraction, e.g., below two percent, or even below a twentieth of one percent, of the total volume as retentate. Preferably, the filter is welded or fastened around its edges to the wall of the vessel by a process such as heat fusing or solvent welding, and covers a region extending from above the port at least down to the port. The vessel may have an upper flange allowing it to drop into a standard concentration tube so that the filtrate leaving the vessel is retained in the concentration tube and may itself be further processed, analyzed or transferred. In one embodiment, a deflectable member or portion of the vessel body operates as a pressure vent between the interior of the concentration tube and the interior of the separation vessel, allowing the vessel to be centrifuged while tightly capped. This feature also adapts a vessel to be overfilled and safely processed in a common tilted rotor assembly without spillage or blowout, thereby increasing the achievable single batch concentration ratio.

The separation vessel may be assembled by positioning a shaped filter sheet within the cone area of the vessel using a tool having one or more heated areas shaped to define bonding segments in peripheral regions of the filter at which the filter is to be fused with the body of the vessel. Preferably, the filter sheet has a trapezoidal shape which curls, when inserted into the vessel, to entirely cover the interior surface of a truncated-cone region of the vessel wall. The vessel may be formed with an alignment rib or other feature along its interior surface positioned to engage an edge of the filter sheet and thus to orient and align the sheet as it is curled against the curved inner wall of the vessel during insertion. A ledge may further be provided to catch the curled, aligned filter in position when fully inserted. Bonding of the filter to the wall is advantageously carried out by supporting the vessel in a heat sink while pressing a hot iron against the inner surface to fuse the filter backing membrane to the vessel wall.

The invention in another aspect provides a centrifugal concentrator having an alignment structure, such as a rib, which extends in a plane through the concentrator tube axis and serves to align a wedge-shaped membrane squarely along the axis during insertion of the membrane and assures that the filter edges are located away from ports of the vessel. The filter may extend substantially the full circumference, so that the well-aligned edges abut and seal precisely when pressed in along the axial direction with a tack welder, such as a conical tip and/or slotted insertion/heat sealing tool. The tool may also melt the vessel rib over the seated butt edges. A seating ledge provided in the vessel wall to engage the top edge of the filter further aids in orienting or positioning the truncated cone filter membrane, and stabilizes filter position during handling or assembly.

In yet another aspect the concentrator tube is configured to fit into and be supported by a filtrate collection tube, and the concentrator tube has a top sealing surface with a deflectable sealing lip that seals against the cap of the filtrate collection tube. The lip deflects in response to outside pressure within the capped collection tube, opening during centrifugation to allow venting via a bypass channel so pressure may vent from the collection tube to the concentrator tube, without leaking or blowing aerosols out to the centrifuge drum. This allows the concentrator tube to be overfilled, i.e., to be loaded into a fixed angle carrier at a higher fill level such that the fluid contents wet the cap, and yet to be processed without spillover or leakage, thus increasing the attainable concentration ratio and enhancing the speed and yield of the concentration process.

The invention also contemplates a separation vessel manufactured with a clamshell construction as part of a vessel array having the form of a strip or row of two or more vessels. In accordance with this aspect of the invention, a sheet of suitable polymer material is formed with a number n of identically-shaped troughs, each trough corresponding to one-half of the desired chamber shape, and including one or more ports formed in a conically sloping region thereof. A sheet of filter material is then placed over the multi-trough polymer sheet, and may optionally be pressed into the troughs and sealingly attached to cover the ports. Attachment is done by advancing one or more tools, such as a press mold or a hot wire die, which advantageously may be advanced in a direction perpendicular to the plane of the sheet, avoiding shear movement at the surface of the filter. A second symmetrically shaped filter-bearing polymer sheet is then laid on top to complete each of the vessel chambers, and the two polymer sheets are bonded together, for example by heat fusion, solvent or ultrasonic welding, or the like, to form a strip of n vessels. The geometry of the strip preferably conforms to the lattice spacing of a standard microtiter plate or multiwell receiving tray, e.g., forms a row of n or m vessels spaced to fit a standard n×m array or rack into which the strip itself is to be loaded for centrifuging. The basic row may also be manufactured to fit a into a portion of a single row or column of the matrix array, allowing multiple different sets of vessel strips to be loaded in the same array, which may, for example have dimensions kn×jm, where k,j are integers.

Advantageously, since each separation vessel or chamber of the assembled array is centered around the tip of the conical region, the retentate resides in a defined and regular lattice position, and is accessible by a direct and unobstructed axial motion, thus making the vessel array adapted to robotic processing, pipette transferor assay, or operations with mechanized handling equipment.

The vessels of the present invention advantageously present a large surface area relative to the effective volume of the vessel, and operate at high rotational speeds while maintaining an open surface filter surface during operation. The filter is broadly supported against the adjacent vessel wall, providing a large flow area via interstitial space for filtrate passing out the ports, and free of internal structural encumbrances that might catch fluid and diminish its efficiency.

Assembly of the vessel and filter membrane is accomplished in a preferred aspect of the invention by insertion of a shaped heating tool to heat peripheral regions of the filter membrane as it lies positioned against the wall of the vessel. The filter may be a regenerated cellulose material on a porous polyethylene backing, such that the tool may contact the cellulosic material without sticking, and melt the backing to the vessel wall. The vessel and filter may be placed between a heat sink, and a press plate, with the heated member contacting the press plate to transfer a defined dosage of thermal energy with controlled thermal characteristics to the weld areas. A superheated rod and thimble embodiment employs a two-step heater advance to preheat and then weld the filter in place. The vessel or press plate may be provided with protrusions or partial ribs to automatically center the heat transfer tooling in the vessel and assure complete welding of the intended weld lines in areas to seal the filter over the ports and prevent ballooning of its central region.

BRIEF DESCRIPTION OF DRAWINGS

These and other features of the invention will be understood from the discussion below and illustration of representative embodiments in the drawings, wherein:

FIG. 7 illustrates a completed separation vessel having a square flange;

FIG. 8 illustrates a strip or cartridge array of separation vessels in accordance with another embodiment;

FIG. 9 illustrates another embodiment of a vessel of the invention wherein a filter membrane extends distally of the outlet port;

FIGS. 11A–11D illustrate another embodiment of a concentrator vessel and filter of the invention;

FIGS. 12A–12C illustrate venting operation of the embodiment of FIGS. 11A–11D;

FIGS. 13A–13F illustrate tools for another manufacturing method and its implementation.

DETAILED DESCRIPTION

In general, applicant's invention contemplates a separation vessel forming a generally elongated or tubular chamber with a conical region in which an ultrafiltration filter membrane allows passage of solvent and lower molecular weight material to an exit port while directing retained higher molecular weight material to a retentate sump. The construction offers a high ratio of filter area to reservoir volume, high filtrate throughput per unit time, and high efficiency of separation of the retained material. By locating the exit port or ports near the apex of a cone, the assembly may maintain a high filtration rate during all or a major portion of the centrifuging separation cycle, and yet isolate a retained faction comprising less than one or two percent of the initial fluid volume. The shape of each filter allows utilization of filter membrane to be highly efficient, with tessellated patterns cut from a large continuous sheet or roll so as to have minimal or no wastage. Further, by mounting the filter to the surrounding wall by perimeter weld along line segments, seventy percent or more of the filter area may be actively used. This will be appreciated from a brief consideration of illustrative embodiment and representative filter shapes applied to conical regions of a ported separation vessel.

Figure 1:
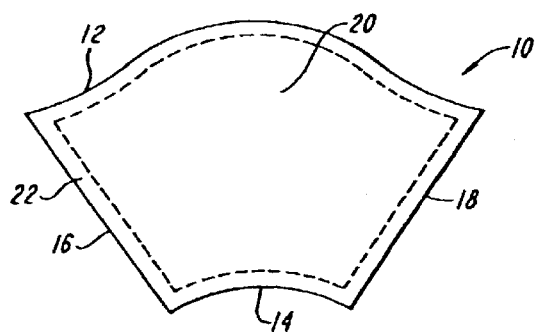
FIG. 1 shows a shaped sheet of filter membrane suitable for the vessel of the present invention.
Figure 2:
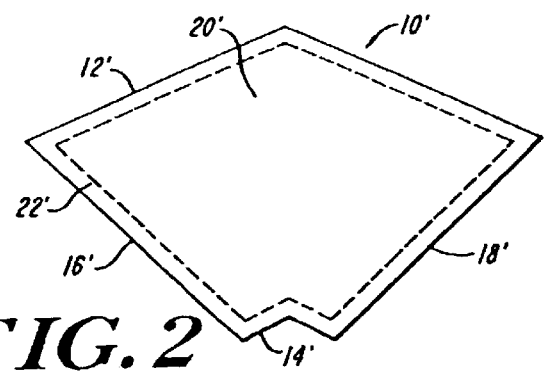
FIG. 2 shows an alternate shape for the filter membrane used in the invention.

Referring to FIG. 1, an exemplary ultrafiltration filter membrane 10 is shown. The filter membrane 10 is of a substantially wedge-like shape, with a proximal end 12 and a distal end 14 and two sides 16, 18. The proximal and distal ends 12, 14 are generally curved or arcuate, while the sides 16, 18 are each substantially straight. The filter membrane 10 has an active area 20 and an inactive area 22. The active area 20 of the filter membrane 10 corresponds to the portion of the filter membrane that, once the filter membrane is placed in a centrifuge tube and sealed, will be capable of ultrafiltration. That is, the active area 20 is that area through which, when the filter membrane is positioned in a separation tube or vessel, the smaller fluid components permeate as the filter membrane is centrifuged. The membrane utilization efficiency of a device design may be calculated by dividing its active area by its total active area, inactive area, and cutting waste area. In the embodiment of FIG. 1, the membrane has an active area of approximately 1.0 $cm^2$ and an inactive area of approximately 0.22 $cm^2$, with no cutting waste area. Thus, the manufacturing efficiency is approximately 0.82 or 82%. This level of efficiency for the wedge-like filter membrane is much higher than the utilization efficiencies of disk-shaped membrane designs currently used in the art. An alternate embodiment of the filter membrane 10 of FIG. 1 is shown in FIG. 2. The filter membrane 10' depicted in FIG. 2 is also of a substantially wedge like design, however, the filter membrane of FIG. 2 has proximal and distal ends 12', 14' that are formed from two substantially straight edges. The sides 16', 18' which connect the ends 12', 14', however, are generally identical to the sides 16, 18 of the filter membrane of FIG. 1. The wedge-like design of the filter membrane 10' of FIG. 2, and its substantially similar dimensions to the filter membrane of FIG. 1 are such that its utilization efficiency is also approximately 82%.

Figure 2A:
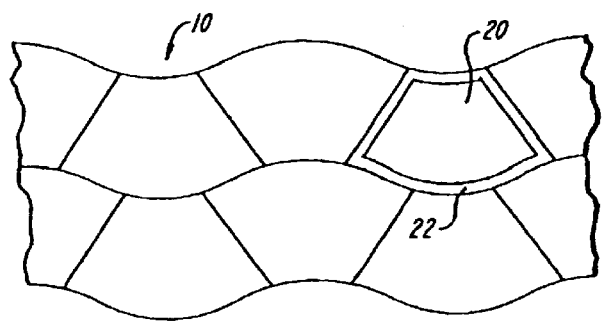
FIGS. 2A and 2B illustrate cutting patterns for obtaining the membranes of FIGS. 1 and 2 respectively from large continuous sheets.
Figure 2B:
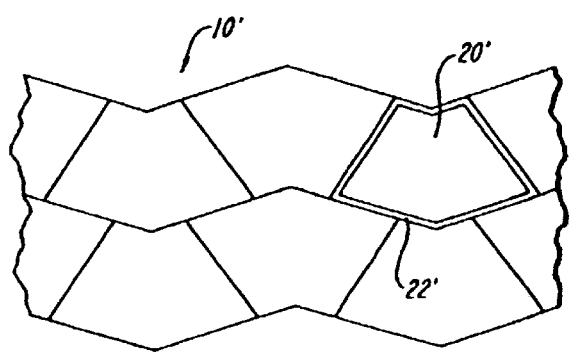

As depicted in FIGS. 2A and 2B, the filter membranes of FIG. 1 or FIG. 2, respectively, may each be laid out like tiles along a strip, facing in alternating directions and be cut without cutting wastage from filter membrane strips which have previously been slit by rolling dies to form the shapes outlined above. One of ordinary skill in the art will appreciate that the filter membrane shapes of FIG. 1 or FIG. 2 may be varied, and also that other filter membrane shapes may be used with the present invention, while still enjoying its attendant advantages. Generally, however, the membrane 10 or 10', regardless of its exact shape, should have a thickness and pore size such that it is able to retain globular solutes having a molecular weight above a threshold, e.g., of at least about 10,000 Daltons. For DNA purification or concentration, the membrane 10 or 10' preferably should have a pore structure rated to retain globular solutes at least above about 30,000 Daltons, to above about 150,000 Daltons.

Figure 3:
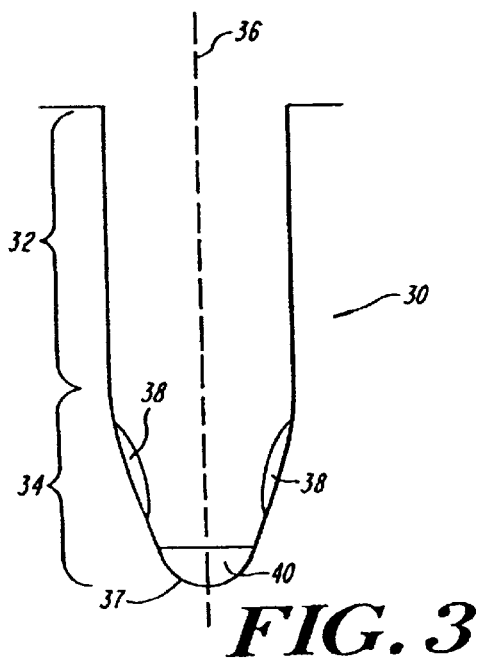
FIG. 3 illustrates a first embodiment of a separation vessel in accordance with the invention.

Referring now to FIG. 3, a reservoir body 30 or concentration tube of the present invention in which a filter membrane 10 or 10' of FIG. 1 or 2 is placed. The reservoir body 30 is generally a tube which has a proximal portion 32 and a distal portion 34 and a longitudinal axis 36. The proximal portion 32 of the tube 30 is cylindrical, e.g., with a substantially constant diameter, while the distal portion is substantially conical and tapers to a closed tip 37. The distal portion 34 of the tube 30 includes at least one port area 38. Preferably, the tube 30 includes two to four port areas 38.

An exemplary tube 30 for use with the present invention resembles a conventional microcentrifuge tube made of polypropylene, which holds about 0.6 milliliters of material and can, in turn, be accommodated in a larger microcentrifuge tube of between about 1.5 and about 2.0 milliliters capacity. The tube 30 may be centrifuged at a wide range of angles and forces. The tube is preferably formed to withstand up to 20,000 G of force. The tube may be used in a 45° fixed angle rotor, or may be placed in an aperture of a fixture in a rotating platform device. The tube 30 may have a longitudinal length of between about 1.0 and about 5.0 centimeters, of which all but about 0.5 centimeter lies above the port areas 38.

The port areas 38, however many are included, are generally identical in their contour and may be located at the same or at varying height along the longitudinal length of the tube 30 they affect. As described more fully below in connection with FIGS. 4 and 5, the filter membrane 10 mounts in the tube 30 with a large area filter oriented so as to be both substantially aligned to the centrifugal force vector, and to cover the port areas 38. Although not herein illustrated, the present invention also contemplates the utilization of differently-shaped tubes including, but not limited to, substantially cylindrical tubes, or tubes which are entirely conical, lacking any proximal portion 32, and which have essentially the entire wetted wall area other than tip 37 covered by a filter membrane.

The distal portion 34 of the tube 30 includes a closed end retentate area 40 in which desired retentate is isolated with high efficiency and may be retrieved without filtering to dryness. As shown in FIG. 3, the retentate area is located partially or entirely distal to the port areas 38, depending upon the angle at which the axis 36 is aligned to the centrifugal force vector. The retentate area 40 should be shaped and placed such that a predetermined amount of desired retentate will remain, and may be removed as is generally known in the art, such as by pipetting or through a robotic or otherwise automated device. For example, in a vessel of 0.6 mL capacity, the ports may be positioned at a height to define a retentate volume 40 of two to twenty microliters.

Figure 4:
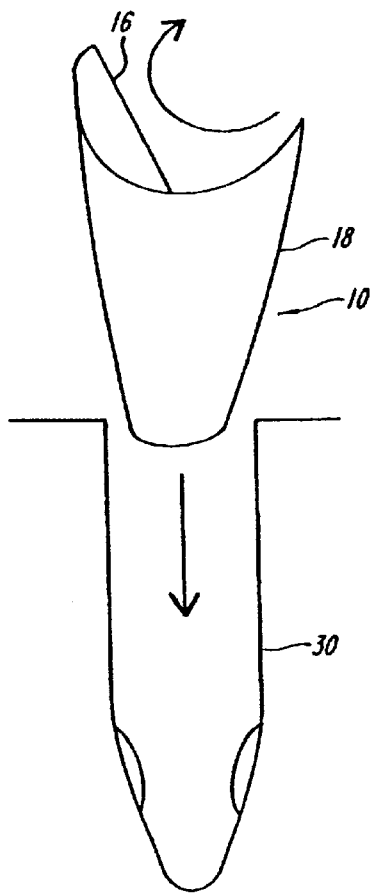
FIG. 4 illustrates assembly of a filter into the vessel of FIG. 3.

Referring now to FIG. 4, the filter membrane 10 of FIG. 1 is shown during assembly being placed in the centrifuge tube 30 of FIG. 3. The edges of the filter membrane 10 are curled over so as to fit within the tube 30. Because of its wedge-like design, the membrane is substantially self-guiding. Specifically, once the narrow tip of the membrane 10 is introduced into the tube, and as it is moved through the entry toward the distal, conical portion 34 of the tube 30, the membrane will curl over into a well aligned frustoconical shell which conforms to the shape of the distal, conical portion of the tube, such that its sides 16, 18 come together and its ends 12, 14 each form a complete circumferential edge.

The membrane 10 may be introduced into, and moved distally throughout, the distal portion 34 of the tube with any suitable or appropriately shaped rod, mandrel, fork or the like. The membrane may be introduced into the distal portion 34 of the tube 30 with the same instrument that is to seal the filter membrane as discussed below. Although not specifically shown in FIG. 4, the membrane 10' of FIG. 2 may be similarly introduced into, and moved distally throughout, the distal portion 34 of the tube 30.

Figure 5:
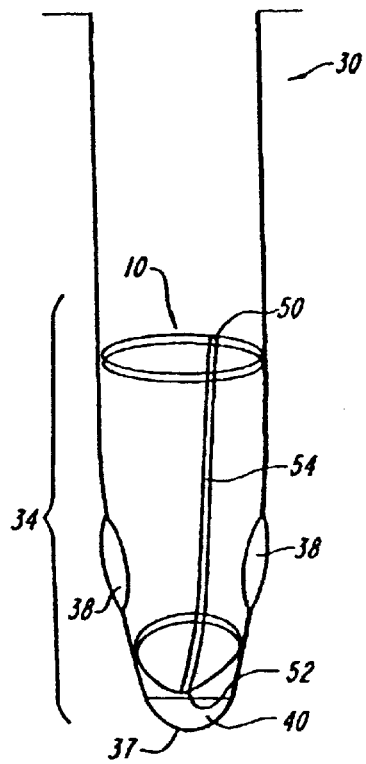
FIG. 5 illustrates another step of assembly of the vessel of FIG. 3.

Once it has been moved distally into a predetermined location in the distal portion 34 of the tube 30, the membrane 10, which may optionally be securely maintained in position by applying a vacuum to the outer surface of tube 30 to draw it snugly against ports 38, (or by applying such a vacuum internally of the tip of an insertion mandrel), is then sealed to the tube around its circumference. As shown in FIG. 5, generally there are three bands of sealing of the membrane filter: a proximal seal portion 50, a distal seal portion 52, and at least one vertical edge sealing portion 54. The filter membrane 10 may be sealed in a number of ways, for example with adhesive or a heat melt polymer in or along the inactive area 22, or by heat fusing with the vessel body in that area. Regardless of the sealing technique, however, the filter membrane 10 should be sealed to the tube 30 around the inactive area 22 such that the filter membrane entirely covers the port area(s) 38, and allows material to exit the tube only through the filter and then through the port(s). Further, the extreme distal end of the filter membrane 10 may extend to and be sealed immediately distal to the port area(s) 38, or it may extend further, into the retentate area 40.

Figure 6:
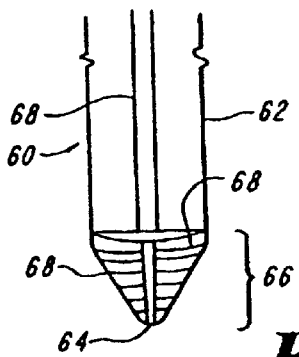
FIG. 6 illustrates one embodiment of a heat welding inserter tool for carrying out the step of FIG. 5.

The filter membrane 10 may be sealed by a heat-welding inserter tool 60 as shown in FIG. 6. As noted above, the inserter 60 preferably has an elongate handle 62 and a conical tip 64 shaped such that the inserter is capable of introducing the filter membrane 10 to the distal portion 34 of the tube 30 and pressing the filter membrane outward against a wall of the distal portion of the tube prior to sealing the filter membrane thereat. Further, the inserter 60 should be shaped, and the filter membrane 10 should be made of a material, such that the filter membrane may be sealed by the inserter 60 without cracking or scratching the membrane and without sticking to the inserter.

In an exemplary embodiment, the inserter 60 has a distal end 66 that has substantially the same shape or contour as the distal portion 34 of the tube 30. The distal end 66 of the inserter 60 also includes, at its surface, a plurality of heater wires or ribbons 68 that also are energized by conductors contained within the handle 62 of the inserter. These wires or ribbons 68 may be Nichrome wire or ribbons, or ceramic ribbon bands which are electrically powered to heat a defined region in order to effectuate a desired seal to the filter membrane 10 in a short time, e.g., approximately two seconds. The surface of the inserter 60 may have features such as a waffle texture, or vacuum passages as well as registration tabs for improved gripping and positioning of the filter membrane 10. Preferably the inserter has a plurality of vacuum passages at the tip, to which vacuum is applied to pick up a pre-cut piece of filter membrane 10. The filter is then inserted to the vessel, and released from the inserter 60 as vacuum is applied externally of the vessel ports to draw the filter securely into position against the vessel wall, where it is then welded, as described above. One of ordinary skill in the art, however, will appreciate that heat may be provided to the inserter 60 using RF or other means, and that its gripping ability may be enhanced in other ways.

FIG. 7 shows a perspective view of a tube 30 with a sealed filter membrane 10. The tube 30 is adapted for placement within a well of a multiwell tray for centrifuging. The proximal region 32 of the centrifuge tube 30 includes a flange 70 which may be any shape suitable to allow the tube to be inserted into an individual well or a multiple well container for centrifuging. In the embodiment shown in FIG. 7, the flange 70 is substantially square.

The tube 30 of the present invention may be used in any conventional individual or multiple well centrifuge, with such multiple well centrifuges including, but not limited to, rotating platform devices. A plurality of centrifuge tubes 30 (one, two, or as many as needed) of the type shown in FIG. 7 may be separately placed in a multiple well carrier. This carrier may then optionally be placed above a receiver multiwell tray 85 (FIG. 10D) used to quantitatively collect filtrate which drips from the bottom point of tip 37 of each tube resting inside the mating receiver well below it. More generally, the tubes 30 may be manufactured as strips or cartridges 80 of eight (see FIG. 8) or twelve tubes, so each strip fills a row or column of a conventional 96-well plateholder. One of ordinary skill in the art, however, will appreciate, that tubes 30 of the present invention may be used in any multiple well centrifuge, regardless of the number of tubes or the matrix orientation of the multiple wells. Furthermore, special adapter plates may be formed, for example, to place four or more such tubes 30 in a larger single well so as to adapt the filtration cell to different existing vessels or centrifuges, or to accommodate a convenient batch size.

Also within the scope of the present invention is an array embodiment, wherein a strip 80 containing a plurality of chambers is made by welding or otherwise bonding a sheet or individual wedges of membrane 10 to two molded halves along the axial plane 75 as shown in FIGS. 10A–10D, treating or cutting away excess membrane at "e" between the tubes if needed to assure dependable joining or sealing, and then welding together the halves to form an integral strip in which each well half has two vertical sealed edges at 54 formed at or just next to the center plane. In this embodiment, the filter is substantially coextensive with the entire wall of the vessel, so, as shown by the meniscus line 76, essentially the entire chamber surface area participates in filtration.

The tube or tubes 30, 80 of the present invention are shaped so that their placement into an individual well centrifuge, or into the strips or cartridges of a multiwell centrifuge, may be performed by a robotic or another automated device. Similarly, the unobstructed axial position of the retentate well permits addition of sample material and removal of the retentate from the retentate area to be performed by a robotic or other automated device. Optionally, retentate may be analyzed directly in the retentate area using multiwell fluorimetry, spectrophotometry, or luminometry. Moreover, the present invention may be adapted to perform diafiltration.

In this regard, the configuration of a filter membrane which is sealed about its ends to a ported tube with a conical end advantageously places the desired retentate in a small, central, distal region, which is both on-axis, and is displaced from the filter membrane. Thus, a pipette may accurately reach the retentate without touching the filter membrane. The cone itself preferably has an apex angle of about 10° to about 35°, and most preferably of about 10° to about 20°, such that the surface of the filter membrane in this region lies at a steep angle of only about 5° to about 10° with respect to the centrifugal force vector. This promotes a continuous sloughing of the denser gel-like, higher molecular weight retentate material that builds up on the filter surface, to efficiently channel that retentate centrifugally down to the apex. Furthermore, by minimizing accumulation of polarized retained macrosolutes, a higher flux rate and minimal retention of smaller molecules is achieved throughout the centrifuging cycle.

FIG. 9 illustrates an alternate embodiment 30' of the tube 30 of FIG. 3, in which a filter membrane 10' extends somewhat distally to the port area(s) 38. This advantageously increases the area 20 of the portion of the filter membrane 10' which remains active toward the end of the centrifuging cycle when approaching the desired retentate volume. Further, this extension beyond the port produces hydrostatic deadstopping, which, in turn, results in a faster approach to the desired volume, by a mechanism such as described more fully in U.S. Pat. No. 4,632,761 of Bowers et al. Alternatively, the distal seal portion 52 may be situated essentially at the level of the sill of the distal-most port 38. In this case, deadstopping is provided solely by sequestering, i.e., by the isolation of the retentate in the small, cup-shaped apex of the tube 40.

When the described embodiment is made with a 0.6 milliliter microcentrifuge tube and is spun on a rotating platform device, the final retentate volume is approximately 0.006 milliliters. When spun in a fixed angle 45° rotor, the retentate volume is about 0.002 milliliters. As can be seen from the approximate scale of FIG. 9, approximately 75 percent of the 0.6 milliliter volume of the tube lies above the proximal seal portion 50 of the filter membrane 10', so that the 1.0 cm$^2$ area of this design, which is twofold larger than prior art devices of this volume range, thus results in an exceptionally high ratio of filter membrane active area to fluid volume throughout the course of volume reduction. This is expected to enhance the speed of protein ultrafiltration by a factor of at least two over that of known devices. Further improvement in protein filtration rate, particularly at transmembrane pressures in excess of 150 psi which are obtained when the device of FIG. 9 is centrifuged above 12,000 rcf, will result if the inner wall of tube 30 in the region adjacent the active membrane area 20 is molded with a rough textured pattern which provides microchannels for filtrate to flow laterally, along the interstitial space between the membrane and the wall, to the port or ports. The device shown in FIG. 10 advantageously has three times the filter area of the embodiment of FIG. 9 and a two-thirds greater sample volume capacity, thus further increasing both the throughput and the speed of DNA diafiltration. Further, the cellulosic membrane covers all portions of the plastic chamber walls except the tip, effectively preventing adsorptive loss of DNA to the surface of the polymer vessel wall. In addition, as described above in regard to FIG. 9, the filter may be positioned for hydrostatic deadstopping to more quickly reach an endpoint. With this enhanced cycle speed, it becomes efficient to reach a desired degree of purity, for example, to effectively remove PCR primers, by simply performing successive diafiltration cycles. The device thus provides a new and effective method for use in DNA amplification to remove unused primers and harvest the PCR product after amplification.

In this regard, it has been reported (Amicon Publication 304) that optimal retention of PCR DNA product larger than about 500 bp and clearance of smaller oligonucleotide primers using YM-100 regenerated cellulose membranes in the Centricon® 100 device requires filtration velocities of no more than one millimeter per minute. The present device of FIG. 9 has threefold greater active surface area than any currently available microcentrifuge device that employs the regenerated cellulosic membranes needed for high recovery of DNA, and thus may be expected to result in as much as a threefold reduction in the time required to diafilter DNA at one millimeter per minute.

In one preferred embodiment of the present invention, the filter membrane 10 is formed of a two-layer filter medium including an inner regenerated cellulose ultrafilter cast on an outer porous film of ultra-high molecular weight microporous polyethylene (UHMWPE). One suitable material is a material sold by Millipore as their PLCCC, PLGCD, PLCGC, PLCTK, or PLCHK filter sheet material which is used in purification systems and has been found to retain globular solutes having an average molecular weight over 5,000, 10,000, 30,000, 70,000 or 200,000 Daltons, respectively. Another suitable material is a regenerated cellulose on Freudenberg or Tyvek backing, such as the material available from the Kalle company in Germany, or available from the Amicon Division of Millipore as their YM line of membranes.

The regenerated cellulosic membrane does not melt, while the polyolefin backing material of the membrane has a higher than or similar melting point to conventional polypropylene microcentrifuge tubes, and compatibly self-welds thereto. This property permits simple and clean device fabrication with a heated conical inserter 60 as described above. Advantageously, after heat-welding the filter membrane 10 against the tapered conical vessel wall surface, the tapered inserter 60 itself, when withdrawn, pulls away from, rather than along, the non-adherent, inner (e.g., cellulose) surface of the filter membrane. Thus, axially press-welding the membrane with a heated tool in this fashion produces no surface abrasion, and the delicate filter membrane skin surface is not damaged. That is, the geometry of contacting along a conical surface results in the tool retracting along a surface release direction, avoiding shear or tearing of the delicate filter material. Prototype testing of this technique showed remarkably high filter integrity, demonstrating manufacturing feasibility.

The advantageous filter rate and efficiency properties noted above are also achieved with the filter membrane 10 also positioned in or extending to the cylindrical portion of the separation tube 30. In such a case, the conical tip 37 of the tube 30 may be made shorter, while the cone angle may be larger, or the tube may otherwise be configured to hold the desired volume of retentate. In each case, the filter membrane extends over and is supported by the peripheral wall of the vessel. This construction using a filter over the perimeter wall may also be applied to cylindrical centrifuge tubes or to purely conical tubes as mentioned above. In each case, a relatively large filter is primarily supported by solid wall, providing a high ratio of active filter area to reservoir volume, while small ports provide escape for the filtrate.

In providing a concentration vessel wherein the filter is coextensive with a region of the peripheral wall and the retentate is captured in a conical tip, applicant's vessel may be seen to both increase the available area and openness of the filter while allowing effective recovery of extremely small volumes with high efficiency. The ratio of sample volume to retentate volume may be controlled by the relative height of the permeate ports and the provision of increased sample volume in the proximal cylindrical portion of the reservoir. Furthermore, selection of the effective membrane pore size allows a high degree of control over the ultimate percentage recovery and required spin down time.

The vessel of FIG. 9 may be implemented in standard sizes identical to those of existing concentration or sedimentation tubes. For example, that device can be configured using a commercial 0.6 mL microcentrifuge tube to form the retentate reservoir. This size tube can be accommodated in a one-and-a-half to two ML filtrate tube for use with small numbers of samples in a conventional 45° fixed-angle microcentrifuge. Alternatively, the same basic device may be arrayed in 8×12 racks above a 96 well microtiter tray used with a swinging platform rotor. As noted above, the open conical retentate well is suited to robotic sample addition and retentate harvesting using conventional laboratory robotic equipment. Furthermore, with a 0.6 mL sample volume and a five microliter retentate sump, the concentrator achieves concentration by a factor of over one hundred.

However, scaling up the vessel size encounters several significant limitations if the larger vessels are to be compatible with existing centrifuge equipment. Thus, for example, if a similar tube is to be used with a standard 15 mL sample or sedimentation tube, the reception of filtrate below the retentate sump imposes limits on the size of the microcentrifuge vessel and its contents, whereas if one were to use a 50 mL tube, the lower rotational speeds of the required large capacity centrifuge would significantly limit separation speed of devices using smaller pore size filter membrane to retain molecules in the range of 5,000 to 20,000 Daltons.

Figure 12A:
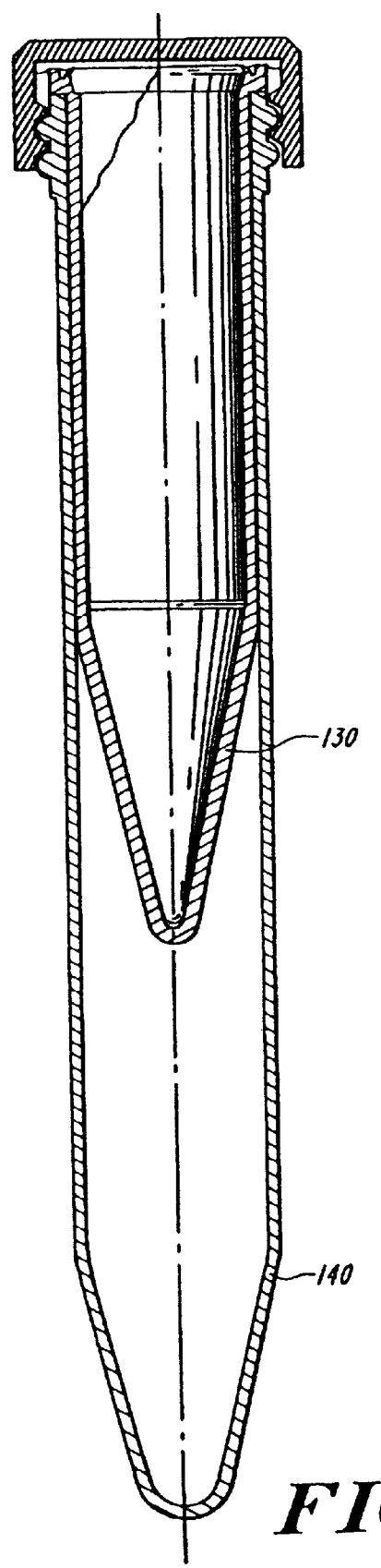

Applicant addresses these limitations in a further embodiment of the invention illustrated in FIGS. 12A–12C, to provide a larger effective batch size while achieving a an even higher concentration ratio, over 2000:1, that is suitable for concentrating extremely dilute samples or for improved diafiltration.

FIGS. 12A and 12B illustrate a 7 mL centrifuge tube 130, constructed in accordance with this embodiment of the invention, and positioned within a 15 mL sample tube 140 of conventional type and having a closure cap or lid 141. As shown, when the assembled pair of vessels reside in a 28° rotor, 6.06 ml. is the maximal volume of filtrate that may pass into the receiver vessel 140 before reaching the same height as that of the hydrostatic dead stop in the retentate area below the port of vessel 130, when that port is positioned to define a three microliter retentate sump. Furthermore, as shown in FIG. 12A at the same angle, when the microcentrifuge vessel of seven milliliters total capacity is filled to 5.2 mL or more, the meniscus in an angled rotor will be at or above the top of the inner vessel 130 (the right-hand side as shown). Thus, the volume of sample accommodated in the microcentrifuge tube as well as the volume of filtrate which must be accommodated in the receiving vessel below the tube both clearly impose limits on the amount of material which may be processed in the vessel without spillage of sample or decanting of filtrate, and these limits are decreased when using a fixed angle rotor. For the illustrated three microliter retentate volume, the concentration range achieved by the vessel is 666:1 from a 2 mL sample, and rises to 2333:1 from a 7 mL sample. Thus, the limitation of 5.2 mL imposed by the spill line (FIG. 12A) of the centrifuge tube limits the achievable concentration to an intermediate value of about 1733:1.

Applicant addresses this limitation in the further embodiment of the invention by providing a separation vessel for fitting within a larger receiving tube having a cap, and wherein the separation vessel is configured with a check seal operating as an internal relief vent to both retain overfilled sample under resting oblique orientation and the high pressure conditions during initial centrifuge operation, and to cycle air pressure from the filtrate chamber to the retentate chamber under the negative pressure conditions that arise as the sample level subsides in the separation vessel and pressure rises in the receiving tube during centrifuging.

FIG. 12C shows an enlarged sectional view of a preferred implementation of this releasing seal construction in the separation vessel 130 of FIG. 12B. As shown, the outer wall 131 of vessel 130 extends upward to a flange 132 that rests upon the body of the receiving vessel 140. The receiving vessel 140 is closed by a cap 141 having a seal gasket 142, and the flange 132 of the separation vessel 130 extends to a top surface 134 which bears against the gasket material 142. This may be a compressible urethane foam gasket material in the cap 141. As shown in the detailed enlarged view of FIG. 12C, the upper surface 134 of the separation tube comprises a check seal lip 134a extending upwardly at an inwardly-directed angle against the gasket to form a fluid-tight band closing the top of the separation tube 130 against the gasket. The lip 134a is sufficiently thin and is disposed at an angle so that, as pressurized air is forced up between the outer wall 131 of the separation vessel and the inner wall of the surrounding receiving tube 140, the increasing pressure deflects the lip 134a downwardly, thus allowing air pressure to pass from the vessel 140 into the separation tube 130. For this operation, a molded bypass passage, best seen as passage 212 in FIGS. 11B and 11C communicates between the surrounding vessel and the space surrounding the lip 134a. As shown in FIG. 12A, this seal arrangement allows the separation tube 130 to be overfilled, that is, to be filled to such a high level that when the tube 130 is placed in a tilted rotor it wets a substantial portion of the gasket 142 lying above it, and the lip seals against the relatively high outwardly-directed pressure that initially develops in that area during rotation at high speed before the fluid level drops, without leaking out of the vessel 130 into the receiving tube 140, or leaking outside the cap into the centrifuge drum. The separation tube may therefore be loaded to a 7 mL capacity rather than the lower, angled overflow level of 5.2 mL, thereby achieving 34% greater effective reservoir capacity and a correspondingly increased concentration ratio of 2333:1. For this purpose, tube 130 is used in cylindrical receiving tube of larger capacity than the existing commercial 15 mL tube of FIGS. 12A, B. For example, a receiving tube such as tube 240 modified as illustrated in phantom in FIG. 11C having a geometry effective to hold 7 mL of filtrate below the port of the vessel 130 at the rotor tilt angle allows the enhanced capacity of the vented filter vessel 130 to be fully exploited in a fixed angle rotor. Such a receiving vessel may be accommodated with simple modifications to existing rotors or fixtures. The cap gasket may be formed of a higher modulus material than the polymer conventionally used in centrifuge tube cap gaskets to achieve, in conjunction with the deflectable lip, a suitable positive pressure sealing and negative pressure release characteristic.

As further seen in FIG. 12C, the outer portion 134b of the rim of vessel 130 seats firmly against the cap gasket 142, while the bottom circumferential edge 134c of the flange 132 seals against the top of the collection tube 140, thus providing a double seal to prevent leakage out of the collection tube 140. The illustrated seven milliliter vessel may have a filter with an area of 5.5 $cm^2$, allowing fast spin-down times to be achieved with the enhanced batch size.

It bears emphasis that the separation vessels and methods of the present invention involve operation at very high rotational speeds, and it is therefore necessary that the filter be well attached to the underlying vessel wall so as to avoid any potential leakage paths, and also be well supported by the wall to prevent sagging and membrane rupture. Preferably, the inner wall of the separation vessel is formed with a rough surface, so that while it supports the filter over its full area, it also permits filtrate to flow or percolate between the outside of the filter and the inside wall of the vessel. Effectively, retentate sloughs off the inner wall of the filter to the sump, and filtrate seeps along the outer wall to the ports, thus keeping both the filter and the filtrate flow paths open.

Figure 11A:
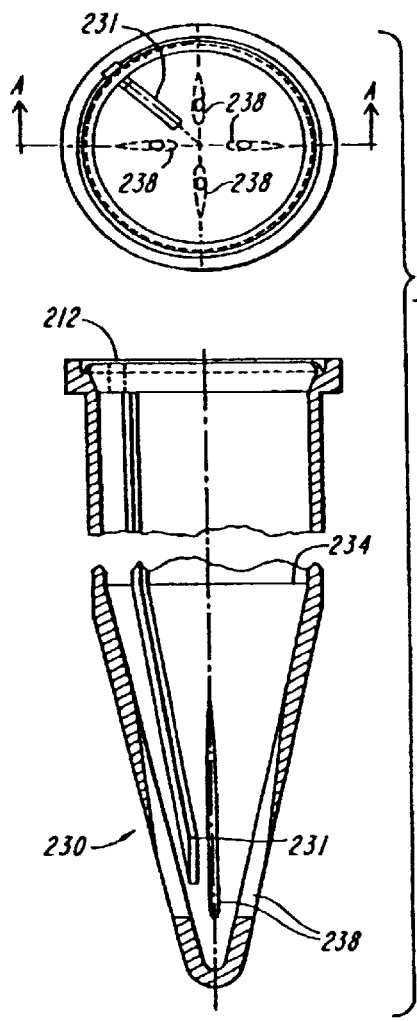
Figure 11B:
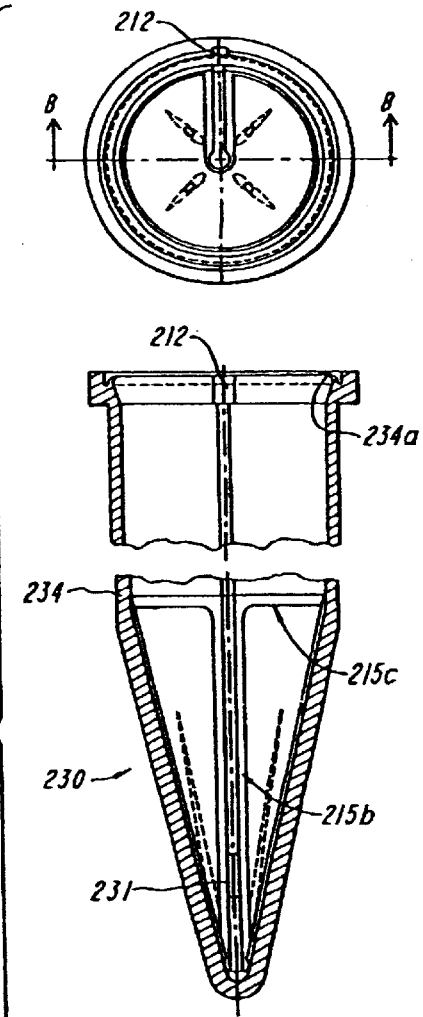

For installation of the filter membrane against a conical surface of the vessel, applicant further contemplates that inner surface of the separation vessel be provided with one or more alignment structures, as illustrated in FIGS. 11A–11C. These figures illustrate the bare vessel (FIG. 11A), its assembly with a filter membrane (FIG. 11B) and the completed separation vessel mounted in a receiving tube (FIG. 11C). Each figure includes a downward facing top plan view, illustrating orientation or relative position of the components of the vessel such as ribs, port and sealing lip, and also includes a vertical section along the plane identified in the corresponding top view.

FIG. 11A illustrates a top view (upper panel) and vertical section side view of a separation vessel 230 such as the vessel of FIG. 12 illustratively having a seven milliliter capacity. As best seen in the top views, the vessel has four ports 238 equispaced about its circumference, and further includes an alignment guide having the form of a rib or blade 231 that projects radially inward from the vessel wall along a diametral plane. Rib 231 is shown extending from near the mouth (top) of the vessel 230 to a position slightly above the bottom of the ports 238. Further the rib 231, which may, for example, be approximately one-half to two millimeters wide, is positioned in a sector between the ports and extends radially to form an elevated wall that catches and aligns the edges 210a, 210b of the filter membrane 210 (FIG. 11D) as it is inserted in the vessel. The membrane 210 preferably is sized or subtends an angle such that the filter edges 210a, 210b butt against the rib on each side of the rib, and the filter 210 bows outwardly in alignment against the vessel wall. As illustrated, the membrane is adhered to the vessel wall along edges 210a, 210b by sealing bands 215a, 215b, respectively, and is further attached at the top and bottom edges 210c, 210d by perimeter sealing bands 215c, 215d. Preferably, the vessel 230 also is formed with a circumferential ledge 234 formed by an indentation of the vessel wall at a height to capture, align and retain the membrane as it is initially inserted into the vessel. That is, the upper edge snaps into position below the ledge 234 after the filter has been inserted down to a level that covers the ports 238. This fully stabilizes and positions the filter, allowing adhesive (if used) to set, or allowing a fusing or welding tool (if used) to be inserted and moved to join the filter to the vessel wall without risk of dislodging or misaligning the filter.

Advantageously the sealing bands 215a–215d occupy relatively little of the filter area; preliminary tests indicate that a band 0.5–0.75 mm wide, and having a net surface area of under one square centimeter will dependably seal a filter of five times that area against the wall of the large vessel of FIGS. 12A–12C discussed above. Additional sealing bands a, b, c as illustrated in phantom in FIG. 11D may also be provided to secure the central region of the filter to the vessel wall and prevent ballooning caused by the weight of the filter as the filter area becomes uncovered in approaching the final deadstop volume.

As noted above, the installation of filter membrane in the vessel 130 requires sealing of the filter to the vessel wall around a peripheral area without damaging the filter itself. It is desirable that this operation be highly automated for the manufacture of the concentration vessels of the invention. For this purpose, impulse welding with a shaped mandrel having heat actuated wire or ribbon element as described above may be used to selectively apply heat while quickly cooling down after the fusing operation. Another approach is to use a shaped press iron inserted against the filter. In both cases, the vessel may be supported by an external support to prevent deformation of the vessel.

Figure 13C:
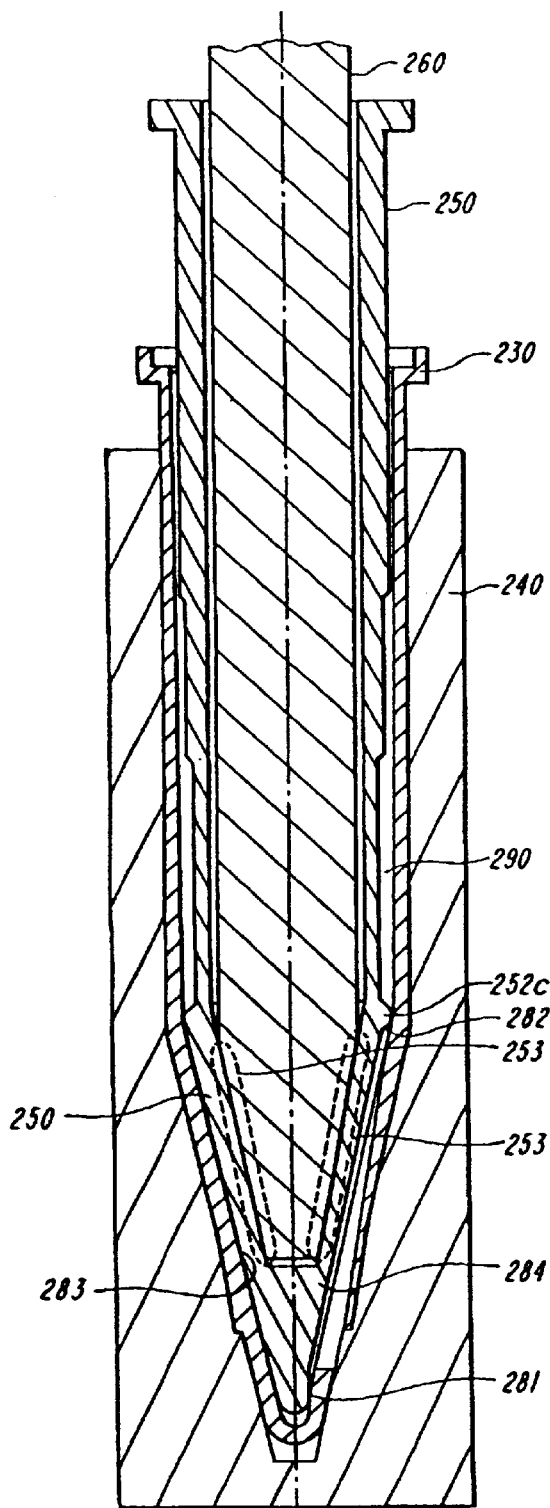

One suitable set of tools for so heat-welding the filter to the vessel and the steps of this operation are illustrated in FIGS. 13A–13F. FIG. 13A illustrates a separation vessel 230, which may be identical or similar to any of the above-described vessels, having a filter membrane 210 positioned therein and covering its port 238. Fastening of the filter 210 in vessel 230 proceeds as follows. The vessel 230 is placed against a receiving heat sink 240 as shown in FIG. 13B. Heat sink 240 may be a heat conductive block of material such as copper and having a recess shaped to receive the vessel 230 and conforming to the region of the vessel 230 at which the filter is to be bonded, e.g., the conical tip. An entry bore permits insertion of the vessel 230, and the entry bore of block 240 is somewhat oversized, providing a small clearance or circumferential relief in the upper access region 241 surrounding the vessel.

A thimble-like or elongated hollow heat transfer tool 250 is then inserted into the vessel along the axis of the vessel down to the tip thereof. The heat transfer tool 250 has a generally elongated shaft portion 251 and a tip portion 252. The tip portion has a conical inner taper, and a thick wall with outer surface protuberances described more fully below, to function as a somewhat thickened hollow thimble element to function as a heat receiving and transfer member, and to press against the filter selectively in the areas to be welded. The outer contour of a welding tip portion 252 is not radially symmetric, but includes vertically running protruding ridge 252a, 252b corresponding to the butt weld of the filter along lines 215a, 215b (FIG. 11D), and may have ridges or bumps in positions corresponding to the tack lines a, b, c of FIG. 11D, as well as a circumferential ridge 252c corresponding to the upper edge perimeter weld 215c of FIG. 11D, and a lower enlarged tip portion 252d which protrudes radially to contact and press the filter against the inner wall of the vessel 230 at the filter's lower edge (region 215d at edge 210d of FIG. 11D). Each of the ridges has steep edges and a well defined upper surface, forming a narrow strip of contact area protruding about thirty mils outwardly of the non-contact portion of the thimble surface. Thus, outside the intended weld lines, the thimble surface has a relief effective to avoid heating the non-weld areas of the filter. The ridges 252a, 252b straddle the centering rib 231 (FIG. 11A), and may for example constitute a single ridge having a narrow slot to accommodate the rib without contact. When the tool 250 is dropped into the vessel, this slot may orient the tool in the vessel. The various ridges, and bumps at tack line positions, further serve to center the heat transfer tool when it is dropped into the vessel, assuring that when a high level of heat is later applied the intended welds will be uniform and the vessel itself will not rack.

The heat transfer tool 250 has a central bore 255 into which a heat applicator rod 260 is then inserted and advanced down to contact the inner wall of the thimble region 252 of the transfer element 250 and transfer heat into the transfer tool wall along its contact region 253. As noted above, this thimble area of the transfer tool has a thin wall, giving it a minimal thermal mass and rapid heating and cooling characteristics. Heat is then transferred to the surrounding filter. The heating rod 260 contacts the thimble intimately, to uniformly and quickly elevate its temperature, but heating of the filter preferentially occurs at the locations of the protruding ridges or bumps on the external surface of the transfer member 250, which are close to, or bear against, the vessel wall. The tip of heating rod 260 fits precisely in the surrounding transfer tool, and each of the tools 250, 260 is independently held at its upper end to allow precise insertion and removal without binding of the two elements of the heating assembly, and to allow removal of the heating rod 260 without upsetting the bonded filter as it cools and sets.

The transfer tool 250 or its tip region 252 may be preheated or warmed a moderate amount before insertion in the vessel 230. However, in accordance with a principal aspect of this assembly method, the heater rod 260 forms the primary heat source and is superheated, i.e., heated to a temperature which is quite high, e.g., hundreds of degrees higher than the melting point of the vessel material or the filter backing, so that it provides a fast and controlled impulse of heat to bring the transfer element up to a temperature above fusing. By way of example, the heater rod 260 may be maintained at a temperature of about 400–475° C. (750–875° F.) for quickly and effectively applying thermal energy to the transfer member 250 when inserted therein. The transfer member 250 may initially start at a low temperature, between ambient and 80° C.

Figure 14:
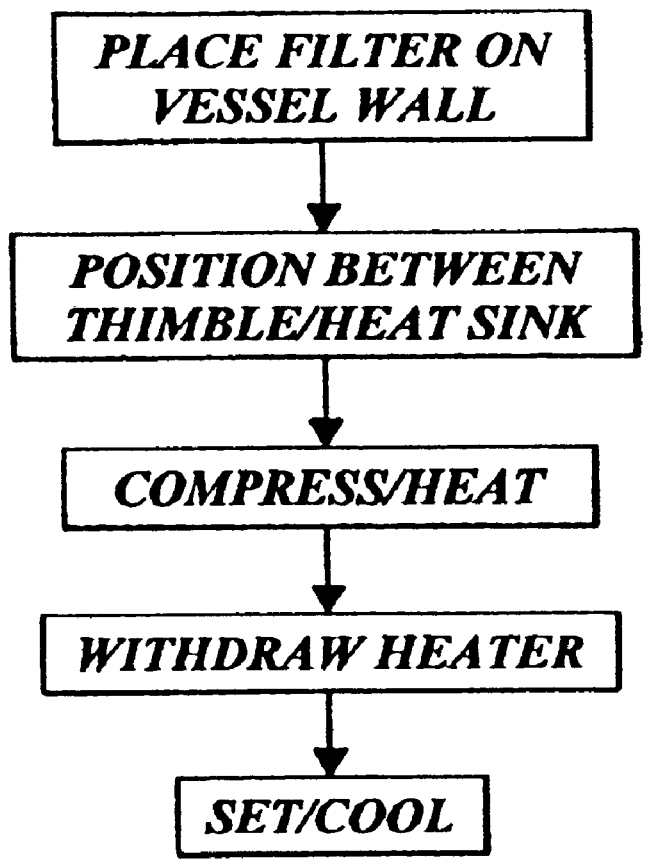
FIG. 14 illustrates steps of the method.

In general, applicant contemplates that the heat welding of the filter in position in this manner is carried out as shown in FIG. 14. First the filter is positioned in the vessel, and the filter/vessel is placed with the transfer tool on one side of the filter while the heat sink supports the vessel on the other side. Welding is then preferably effected in two stages by a preheating stage which may be accompanied by a partial compression of the filter in the areas contacted by the ridges of the transfer tool, followed by a compression and heating stage in which the heat transfer tool is advanced to bear more strongly against the filter to assure continuous fusing along the intended bond lines. The second-stage increased pressure may be applied by advancing the heater rod 260 five or ten mils further and/or applying greater pressure via the heater rod 260, or, equivalently, raising the sink 240 by a small distance. The heating member 260 is then withdrawn and the assembly is allowed to set and cool before removal of the heat transfer tool from the vessel, and removal of the vessel from the heat sink block.

These steps are illustrated in greater detail in FIGS. 13C–13F. As shown in FIG. 13C during the preheating stage, heating rod 260 is advanced into the transfer tool 250 with moderate or slight pressure or compression so that its conical tip lies against the inner wall of the heat transfer thimble 250 and the various protruding ridges or dots 252a, 252b . . . come into contact with the surrounding filter. By way of example, with a filter membrane approximately 10 mils thick, the protruding ridges may compress the filter partially under the edge weld line positions 283 and at circumferential band positions 281, 282, for example by 2 to 5 mils, and the thimble surface otherwise resides above the filter elsewhere as seen at non-bonding region 284 without transferring any appreciable heat thereto. At this stage the non-protruding portions of the heat transfer thimble exterior surface reside ten to fifty thousandths of an inch above the filter surface, so only minor heat is transferred, inefficiently, by radiation or convective means without direct contact or thermal conduction. As a result, the filter is preferentially heated in the bonding areas, so water in the filter material weld regions may evolve as steam and has ample space for escaping in the gap between the transfer tool 250 and the inner wall of the vessel 230 and filter. By way of illustration, the heater rod 260, initially at 740–900° F., may bring the transfer member to about 250–300° F. during the preheating stage for attaching a regenerated cellulose membrane to a polypropylene vessel, and preheating occurs in bonding strips ten to eighty mils wide.

Figure 13D:
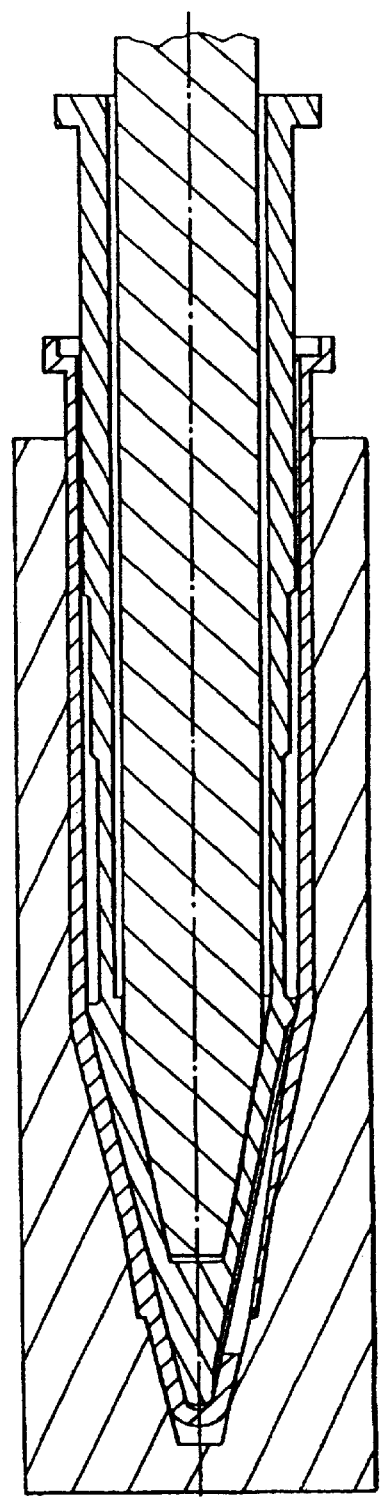

After maintaining the preheating position for several seconds to allow escape of the steam, further pressure or movement is then applied to heater rod 260 or heat sink 240, and the transfer tool and rod advance further into the vessel 260, firmly establishing thermally conductive contact and sealing the filter along the perimeter and other intended weld bands against the wall of the vessel. This welding at full compression is illustrated in FIG. 13D. At this point, the transfer tool temperature may illustratively lie in the range of 350–400° F., while the temperature of the heater rod 260 may have fallen appreciably, e.g., to about 480–600° F. Following closure of clamps 270 to hold the transfer tool, the heater rod 260 is then withdrawn, allowing the temperature of the vessel to fall by heat conduction into the sink 240 and up the shaft of the transfer member 250 into clamp 270, until the bond has set. In this manner a controlled bolus of heat is preferentially transferred into regions of the delicate filter to weld without abrading or injuring the filter itself. The heat transfer tool is then removed and the finished vessel 230 is withdrawn from the heat sink. As seen in FIG. 13F, the bond lines 215a, 215c, 215d, a, b are clearly visible in the completed assembly due to fusing together of the vessel wall and backing material in those areas.

This manufacturing method has great advantages in that the thermal mass of the transfer member 250 and the heating rod 260 are precisely determined, and their starting temperatures and the residence time of the heating rod in the heat transfer member 250 may both be set so that precisely controlled amounts of heat are applied to the filter, both for preheating and fusing, while no actual movement of the filter or shearing motions occur when the assembly is at elevated temperature. The heat sink 240 establishes a sharp thermal gradient through the wall of the vessel, allowing the body of the vessel 230 to remain intact and assuring a fast setting time, while high levels of pressure may be applied to assure complete fusing along the narrow bonding lines and tack-down regions of the filter.

The heating rod 260 may be maintained at the desired temperature by securely mounting it in a larger heated block, for example a copper block maintained at 900° Fahrenheit, and may be instrumented, for example with an internal thermocouple, to conveniently monitor tip temperature and control its reheating or residence cycles. Optionally an internal heating element may be incorporated into the heating rod to shorten thermal recovery time between welding cycles. Moreover, by selectively driving off water from the membrane material to be welded, the process prevents bubble defects from arising in the fused areas, or buckling of the filter, and dries the relevant filter area without impairing the activity of the cellulosic material of the filter media, which remains hydrated without loss of function.

Figures 10A, 10B:
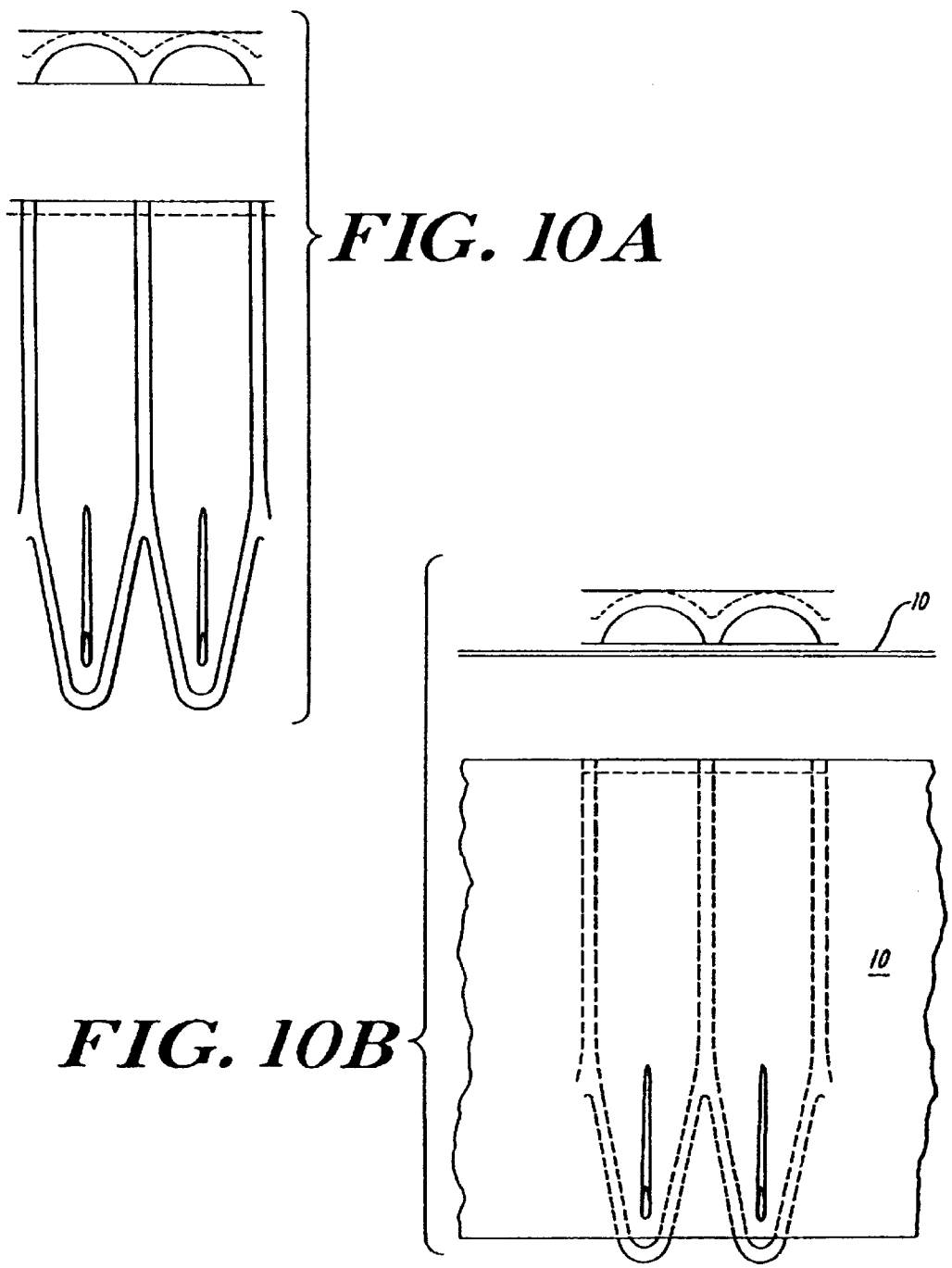
FIGS. 10A–10D illustrate steps of manufacturing and use of a strip array embodiment like that of FIG. 8.
Figure 10C:
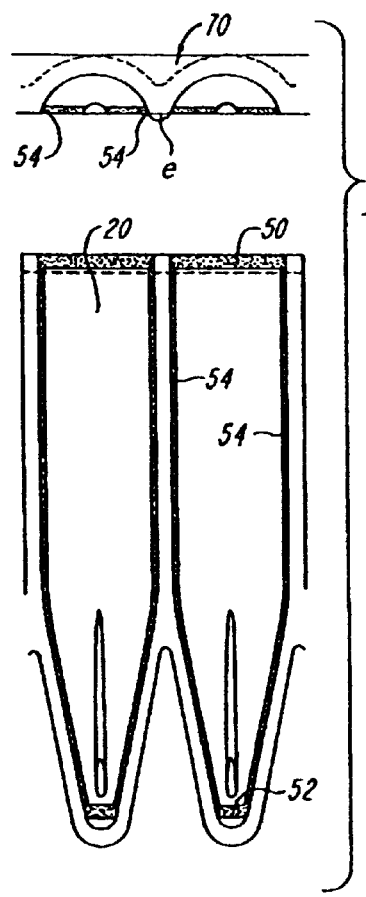
Figure 10D:
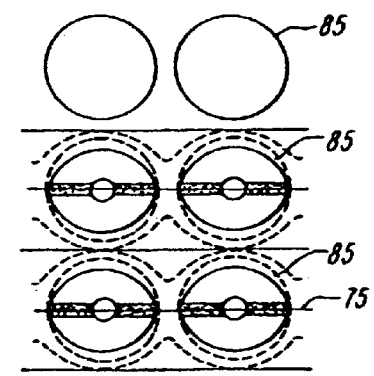
Figure 10D:
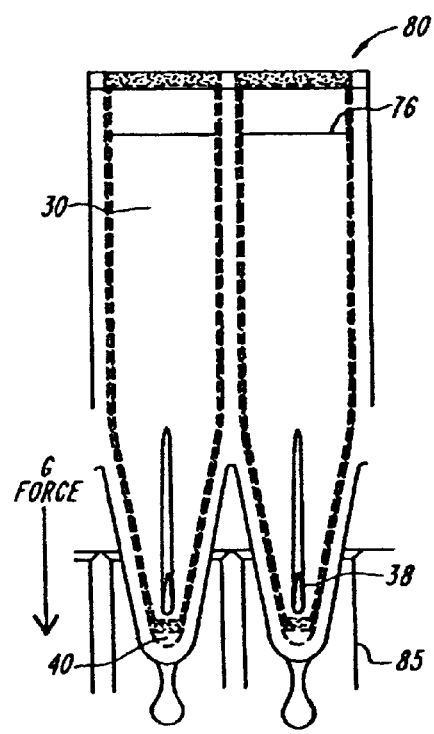

The filter attachment method of FIGS. 13 and 14 may be applied more generally to other geometric configurations, such as flat window figure configurations, or the open curved sheet or clam shell construction of FIGS. 10A–10C. In this case when applied to the multiple half-vessel shells of FIGS. 10A–10C, the transfer member may be a sheet-like member having protruding contour conforming to the general shape of the vessel wall with press-protrusions for effecting the desired welds. The heat applying member, rather than a conical tipped rod, may then be shaped correspondingly, with contact areas conforming to the back surface of the filter pressing areas of the transfer member. In each case, the use of a transfer plate to hold the vessel and filter assembly with minimal movement against the filter surface, and to modulate the heat transfer characteristics of a super heated heating assembly that is temporarily moved into position to initiate press-welding, serves to insure the integrity of the filter while forming uniform and dependable bond lines between the filter and the vessel wall.

One skilled in the art will appreciate further features and advantages of the invention based on the above-described embodiments. Accordingly, the invention is not to be limited by what has been particularly shown and described, but will be seen to include further variations, modifications and adaptations within its scope, as defined by the claims appended hereto and equivalents thereof. All publications and references cited herein are expressly incorporated herein by reference in their entirety.

What is claimed is:

1. A method of attaching a filter membrane to a separation vessel, the method comprising the steps of
providing the separation vessel as a chamber having a curved interior wall and a port on said wall,
providing a wall element of the curved interior wall, said wall element being effective to engage a sheet when placed thereagainst, and
inserting a shaped piece of filter sheet having side edges into the chamber so that the shaped piece is curled by the wall and a side edge is engaged by the wall element to guide the shaped piece into a position of alignment over the port as it is inserted whereby the shaped piece of filter sheet is accurately positioned for attachment inside the chamber to form a separation vessel, and sealing the filter sheet to the wall.

2. The method of claim 1, wherein chamber has a conical portion, and said shaped piece of filter sheet is shaped to cover at least a truncated cone portion of said conical region.

3. The method of claim 1, wherein the wall element comprises a ledge at a position effective to capture the filter sheet at a distal end of the chamber.

4. The method of claim 3, wherein the ledge is formed by forming an indentation of the chamber wall below said position effective to capture the filter.

5. The method of claim 1, wherein the wall element comprises a rib that projects radially inward from the chamber wall along a diametral plane.

6. The method of claim 1, wherein the step of providing a wall element includes providing a wall element that projects radially inward from the chamber wall in a diametral plane, and wherein the step of inserting includes inserting a filter sized such that opposed edges thereof butt against the rib and the filter bows outward against the chamber wall.

7. The method of claim 1, wherein the step of sealing includes a step of contacting the filter sheet with a heated member to seal the sheet to the wall when the sheet is positioned over the port.

8. The method of claim 7, wherein the heated member includes an insertable thimble having an external relieved surface to clear the vessel wall and with protruding surface features in said bonding regions.

9. The method of claim 7, wherein the heated member is heated to a temperature substantially above melt of at least one of said vessel wall and a surface of said filter sheet.

10. The method of claim 7, further comprising the step of applying pressure to the heated member to compress and fuse bond lines fastening the filter sheet to the chamber.

11. The method of claim 1, wherein said chamber has a closed end forming a deadstop having a volume between about 0.3% to about 1% of volume of the separation vessel.

12. The method of claim 1, wherein said filter sheet has a frusto-conical active filter area when positioned and sealed in said chamber.

* * * * *